United States Patent [19]

Wason

[11] 4,272,509

[45] Jun. 9, 1981

[54] PRECIPITATED SILICON DIOXIDE CLEANING AGENT AND DENTIFRICE COMPOSITION

[75] Inventor: Satish K. Wason, Churchville, Md.

[73] Assignee: J. M. Huber Corporation, Locust, N.J.

[21] Appl. No.: 129,773

[22] Filed: Mar. 12, 1980

Related U.S. Application Data

[63] Continuation of Ser. No. 943,884, Sep. 19, 1978, abandoned.

[51] Int. Cl.³ ............... A61K 7/16; C01B 33/12; C01B 33/193
[52] U.S. Cl. ............... 424/49; 106/288 B; 423/335; 423/339
[58] Field of Search ............... 423/335, 339; 106/288 B; 424/49

[56] References Cited

U.S. PATENT DOCUMENTS

| | | | |
|---|---|---|---|
| 3,705,940 | 12/1972 | Kirchgassner | 424/49 |
| 3,960,586 | 6/1976 | Wason | 106/288 B |
| 3,977,893 | 8/1976 | Wason | 106/288 B |
| 3,993,497 | 11/1976 | Wason | 106/288 B |
| 4,067,746 | 1/1978 | Wason et al. | 106/288 B |
| 4,122,160 | 10/1978 | Wason | 106/288 B X |
| 4,127,641 | 11/1978 | Aldcroft et al. | 106/288 B X |

Primary Examiner—Jack Cooper
Attorney, Agent, or Firm—Timothy R. Kroboth; Robert L. Price; Harold H. Flanders

[57] ABSTRACT

A synthetic precipitated silicon dioxide is provided which is an abrasive agent for use in toothpaste or other dentifrice compositions wherein the precipitated silicon dioxide has a controlled particle size, narrow size distribution and controlled functional properties including very low structure and an oil absorption of less than about 60 cc/100 g. The precipitated silicon dioxide provides a product which is more economical to produce than silica xerogels now used in dentifrices, and provides a precipitated silicon dioxide which gives excellent clarity in clear gel dentifrice compositions.

8 Claims, 2 Drawing Figures

PRECIPITATED SILICON DIOXIDE CLEANING AGENT AND DENTIFRICE COMPOSITION

This is a continuation, of application Ser. No. 943,884, filed Sept. 19, 1978, now abandoned.

TECHNICAL FIELD

This invention relates to a relatively large particle size synthetic precipitated controlled structure silicon dioxide which is useful as a cleaning and abrasive agent in toothpaste compositions, and especially visually clear toothpaste compositions, when product provides properties which are comparable to the more expensive silica xerogels now used in such compositions.

BACKGROUND ART

Visually clear toothpaste compositions are well known in the art and are disclosed in many United States and foreign patents. One of the earliest patents in this field is U.S. Pat. No. 3,538,230 to Pader which discloses dentifrice compositions containing as the essential polishing and cleaning ingredient, a synthetic amorphous, porous silica xerogel. A specific example of a silica xerogel is that sold commercially under the trade name SYLOID 63 which is a preferred material in this patent and is used in commercially available toothpaste compositions. The disclosure in U.S. Pat. No. 3,538,230, also states that synthetic amorphous silicas of the prior art, such as precipitated silicas, pyrogenic silicas, and xerogels, are undesirable for dentifrice use, particularly in visually clear toothpaste compositions, either because of their initial small particle sizes or because they break down into smaller particle sizes resulting in poor cleaning ability. See U.S. Pat. No. 3,538,230, column 2, lines 12–17.

A number of U.S. patents have also been recently issued to the present applicant which disclose and claim precipitated silicas, some of which are useful as abrasive agents in toothpaste compositions, including visually clear toothpaste. These patents include U.S. Pat. No. 3,893,840, 3,928,541, 4,076,549, 4,038,098, 3,988,162, 4,015,996, 4,067,746, 3,977,893, 3,960,586, 3,967,563 and 3,993,497. Reference is also made to copending applications of the same assignee including Ser. No. 550,324, filed Feb. 18, 1975 now U.S. Pat. No. 4,105,757, Ser. No. 729,448 filed Oct. 4, 1976 now U.S. Pat. No. 4,122,160; Ser. Nos. 653,718, now abandoned, 653,719 now abandoned and Nos. 653,720, now U.S. Pat. No. 4,144,321, all filed Jan. 30, 1978; Ser. No. 854,165, filed Nov. 23, 1977; Ser. No. 876,284, filed Feb. 9, 1978 abandoned and refiled as Ser. No. 039,062, filed Aug. 11, 1979; Ser. No. 559,476, filed Mar. 18, 1975; now U.S. Pat. No. 4,122,161; Ser. No. 731,481, filed Oct. 12, 1976 now U.S. Pat. No. 4,156,717; Ser. No. 685,512, filed May 12, 1976, abandoned and refiled as Ser. No. 6,153, filed Jan. 24, 1979; Ser. No. 813,323, filed July 6, 1977 now U.S. Pat. No. 4,140,757; Ser. No. 826,901, filed Aug. 24, 1977 now U.S. Pat. No. 4,159,280; and Ser. No. 862,384, filed Dec. 20, 1977, abandoned and refiled as Ser. No. 041,952, filed Mar. 23, 1979. All of these pending applications also disclose precipitated silicas which may be used as components in toothpastes. The products of the present invention, however, have characteristics different from these prior patents and applications, which provide increased clarity. It is advantageous to the art, however, to develop new synthetic precipitated amorphous silicon dioxides which provide characteristics making them suitable for incorporation into visually clear dentifrice compositions as a substitute for the silica xerogels because the precipitated silicon dioxides are much more economical to produce and provide greater clarity than products of the prior art.

SUMMARY OF THE INVENTION

It is one object of the present invention to provide a synthetic precipitated silicon dioxide which is not a xerogel but which has equal or superior cleaning properties to commercially available xerogels.

A further object of the invention is to provide a relatively large particle size, synthetic precipitated controlled structure silicon dioxide which, when incorporated into toothpastes, provides toothpaste clarity which is comparable to, or better than, toothpaste clarity containing the silica xerogels in visually clear toothpastes.

A still further object of the invention is to provide an oral dentifrice composition which can be produced using a novel, synthetic precipitated silicon dioxide which has cleaning and abrasive properties and cosmetic appeal but which can be produced by a very economical manufacturing process.

A still further object of the present invention is to provide a synthetic precipitated silicon dioxide produced by an acidulation process which, when incorporated into a dentifrice composition, provides toothpaste clarity superior to xerogels, but which can be produced by a simple precipitation process which results in the production of a dentifrice containing a precipitated silicon dioxide of significantly lower cost than the comparable xerogel silica.

In satisfaction of the foregoing objects and advantages, there is provided, by this invention, a precipitated amorphous silicon dioxide which has a controlled particle size, narrow size distribution and controlled functional properties and minimal porosity when compared to a xerogel cleaning agent, said precipitated amorphous silicon dioxide having a very low wet cake moisture of less than about 51 percent, a refractive index ranging from 1.45 to 1.465, an oil absorption of less than about 60 cc/100 g, a surface area ranging from about 250 to 375 m$^2$/g, a pour density in the range of about 16 to 19 lb/cu.ft. and a pack density of about 34 to 38 lb/cu.ft.

Also provided by the present invention, is a procedure for the preparation of the synthetic precipitated silicon dioxide which generally comprises the steps of forming a fresh water sodium silicate solution having an SiO$_2$/Na$_2$O mole ratio of about 2.6±0.05 and a sodium silicate concentration of about 15% to 20%; producing an inorganic acid solution having a concentration of about 10 to 20% by weight of acid; forming a solution of an adduct material such as aluminum sulfate; mixing the acid solution and adduct solution to form an acidification agent; charging a portion of the sodium silicate solution to a reactor and heating to 80°–90° C., and then adding the remaining sodium silicate solution and acidification agent simultaneously to the reactor at the indicated reaction temperature at a steady rate until the sodium silicate solution addition is completed, and then continuing addition of the acidification agent to reach a pH of 6.0 or less; digesting the resulting precipitated silica to stabilize the surface area, adjust to the final pH of about 6.0, filtering and washing the precipitated silicon dioxide; reslurrying the filter cake in its own water and adjusting to a desired final pH of 4±1 by addition of acid and drying to constant weight. The resulting filter cake is then milled to the desired degree of fineness and characterized.

Also provided by this invention is a dentifrice composition and more specifically a toothpaste formulation, containing the precipitated silicon dioxide agent of this invention in both opaque and visually clear forms.

BRIEF DESCRIPTION OF THE DRAWINGS

Reference is now made to the drawings accompanying the application wherein.

DESCRIPTION OF BEST MODE OF THE INVENTION

As pointed out above, the prior art is well aware of the use of xerogel synthetic silicas as cleaning and abrasive agents in toothpaste compositions, and particularly in clear gel or visually clear toothpaste compositions. The present invention provides a synthetic precipitated silicon dioxide which is not a xerogel but which possesses equal or superior cleaning properties to the more expensive xerogels. The large particle size synthetic precipitated controlled structure silicon dioxides of the present invention may be incorporated into toothpaste compositions, and will provide a toothpaste clarity equal to or better than toothpaste clarity obtainable with known silica xerogels. Since the precipitated silicon dioxides of this invention provide better or superior cleaning properties, and better clarity in visually clear toothpastes, and are more economical to produce, it is clear that the novel synthetic precipitated silicon dioxides of this invention provide a number of advantages which make them superior to the silica xerogels of the prior art.

A typical silica xerogel which is often used in clear dentifrice products is Syloid ®63. The key properties of Syloid 63, as listed in the supplier's technical bulletin (entitled Davison Family of Syloid Silicas at Work, W. R. Grace Company), are listed below:

| SYLOID ® 63 | |
|---|---|
| Property | |
| BET Surface Area, m²/g | 675 |
| Oil Absorption, lb/100 lb | 60 |
| Bulk Density, lb/ft³ | 29 |

Figure 1:
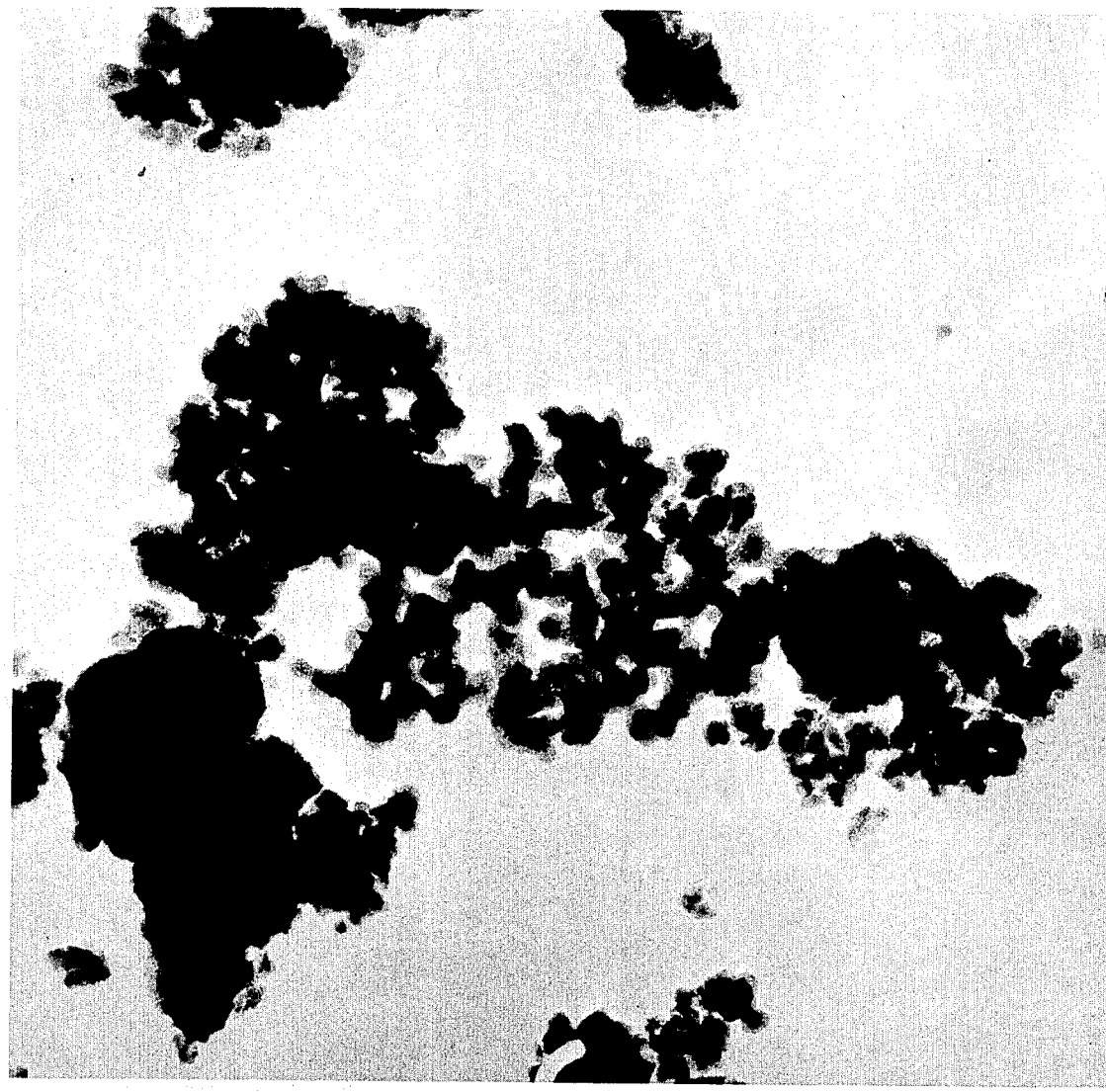
FIG. 1 is a photomicrograph of the precipitated silicon dioxide of this invention at a magnification of 69,800×.
Figure 2:
FIG. 2 is a photomicrograph of Syloid 63 xerogel at a magnification of 69,800×.

The comparative electron photomicrographs of Syloid 63 xerogel and the precipitated silicon dioxide of the instant invention are given in FIGS. 1 and 2. FIG. 2 is an electron photomicrograph of Syloid 63 xerogel and FIG. 1 is an electron photomicrograph of the precipitated silicon dioxide of the present invention.

The examination of FIGS. 1 and 2 clearly shows that the xerogel and the precipitated silicon dioxide of the present invention drastically differ from each other in morphology, particle size, particle shape and porosity. FIG. 2 clearly shows a high degree of internal porosity in the structure of xerogel silica while minimal or no porosity is evident in the electron photomicrograph of the precipitated silicon dioxide of this invention as shown in FIG. 1.

The synthetic precipitated silicon dioxide cleaning and abrasive agents of this invention, have a controlled particle size and narrow size distribution together with controlled functional properties and minimal porosity when compared with comparable commercial xerogel cleaning agents. Moreover, the precipitated silicon dioxides of this invention can be produced by a simple precipitation process which is one of the features of the invention in economic production of the material.

The precipitated silicon dioxides of this invention are characterized by a number of characteristics which are unique to the product and which distinguish them from other precipitated silicon dioxides of the prior art, many of which are contained in applicant's own patents. The precipitated silicon dioxides of this invention thus may be characterized as having a very low wet cake structure which is generally on the order of less than about 51%, and more specifically in the range of about 46.0 to 51.0%. The refractive index of this product is comparable to that of the silica xerogels in that it ranges from about 1.45 to 1.465 at 25° C. and, thus, is in the proper range for incorporating into clear gel toothpaste compositions using standard liquid phase composition ingredients. The oil absorption is a very low oil absorption which is generally below about 60 cc/100 g, preferably about 50 to 60 cc/100 g, which is comparable to the xerogel. It should be understood that most precipitated silicon dioxides known in the prior art for use as abrasive agents in toothpaste compositions, generally have oil absorptions much higher than about 60 cc/100 g and this is another specific feature of the products of the present invention. The surface area of the particles of the precipitated silicon dioxides of this invention is significantly lower than xerogel, ranging from about 275 m²/g up to about 375 m²/g. The surface area is at least above about 225 m²/g. The pour densities of this product are greater than about 16.0 lb/cu.ft. and preferably in the range of about 16.0 to 19.0 lb/cu.ft. The pack density is in the range of 35 lb/cu.ft. and preferably is from about 34 to 38 lb/cu.ft. Preferred classes of products are those wherein the surface area is above 350 m²/g, preferably about 356 to 374 m²/g, and the pour density is about 16.0 to 18.4 lb./cu.ft.

Evaluation of the products of this invention in dentifrice compositions also provide a product with outstanding characteristics. Thus, the RDA values, or Radioactive Dentin Abrasion, as determined by the method of Grabenstetter, Journal of Dental Research 37, 1060, 1958, wherein calcium pyrophosphate is a standard assigned as a value of 500, are at least above 300 and generally in the range of about 325 to 425. This is an outstanding RDA value for precipitated silicon dioxides.

The toothpaste clarity of the silicon dioxide is also important when incorporated into clear gel toothpastes. In general, using the method of the present invention, reproducible silicon dioxides can be produced which have a toothpaste clarity in the rating system of 8 and 9, which is a clear toothpaste, the clarity being equal or superior to commercial toothpastes. Thus, these products provide outstanding clarity when incorporated into visually clear toothpaste compositions as the abrasive and cleaning agent. However, it should be understood that the silicon dioxides of the present invention are also excellent polishing agents in opaque toothpastes.

In present day toothpastes, which utilize a fluoride therapeutic agent, a common problem with storage of such toothpastes has involved a decrease of the fluoride on storage or poor shelf-life. This has been particularly true in toothpastes which are stored in unlined aluminum tubes because of reaction between the fluoride contained in the toothpaste and the aluminum of the tube. Therefore, it has been necessary to provide a toothpaste tube made of an aluminum lined with a lacquer coating in order to incorporate a therapeutic fluoride toothpaste into the tube and obtain reasonable storage or shelf-life without substantial loss of the fluoride therapeutic agent.

The fluoride availability of therapeutic toothpaste is normally referred to as fluoride compatibility. The fluoride compatibility was run by storing dentifrice at 120° F. for one month and then analyzing the free fluoride by the standard fluoride specific ion electrode method. The compatibility values were obtained by dividing the available free fluoride by the total theoretical fluoride in the dentifrice. The compatibility value multiplied by 100 is referred to as percent fluoride compatibility or percent compatibility.

In general, percent fluoride compatibility above about 75% is considered good. The products of the present invention provide a fluoride compatibility of at least above 80 and, more preferably, in the range of about 83 to 88%. This is considered to be excellent fluoride compatibility, and when combined with the dentifrice RDA values, and clarity of the toothpaste, together with its excellent cleaning and abrasive action and low cost, makes the precipitated silicon dioxides of the present invention an outstanding advance in the art.

The precipitated silicon dioxide abrasives of this invention are preferably prepared by charging an aqueous solution of an alkali metal silicate solution, preferably a sodium silicate solution, to a reactor for acidulation. The aqueous sodium silicate solution is a fresh water solution having a sodium silicate concentration range of about 15 to 20 wt.%, and more preferably about 18 to 20 wt.%, and an $SiO_2/Na_2O$ mole ratio of about $2.6 \pm 0.05$ for best results. The aqueous sodium silicate solution is then raised to a temperature of about 50° to 90° C. and with continuous agitation the solution is acidulated by the addition of an acidification agent comprising a mineral acid having a concentration of about 10–20 wt.% which has been mixed with a solution of an adduct material. The addition is at a substantially constant pH in the range of about 8.5 to 10.5.

The acidification agent is prepared from available commercial mineral acid, preferably sulfuric acid which has a concentration of about 93%, by dilution with sufficient fresh water to produce a dilute solution containing about 10% to 20% by weight of sulfuric acid. An adduct solution having a concentration of about 10% to 25% is produced by diluting a commercially available concentrated adduct material with fresh water. The adduct solution is prepared from a soluble salt of an adduct material such as aluminum, calcium, strontium, barium, or mixture thereof, aluminum being preferred. An especially preferred adduct material is aluminum sulfate. Thereafter, an acidulating agent is prepared by mixing the inorganic acid solution and adduct solution. This mixed acidification agent is then used as the acidulation agent in formation of the precipitated silicon dioxides. The mineral acid is preferably sulfuric acid as sulfuric acid provides best results, but as is known in the art (see my U.S. Pat. Nos. 3,988,162, 3,893,840 and copending application Ser. No. 703,496, filed July 8, 1976), other acidulation agents such as nitric acid, phosphoric acid, hydrochloric acid, carbonic acid, and the like, can also be employed.

In the most preferred embodiment, only a portion of the alkali metal silicate solution is charged to the reactor, brought to temperature under agitation, and the acidification agent and remainder of the alkali metal silicate solution simultaneously added to the initial silicate solution at the reaction temperature. Preferably, about 8 to 12 wt.% of the total theoretical alkali metal silicate is initially charged to the reactor. The remaining portion is then added with the acidification agent. The time period over which the alkali metal silicate and the acidification agent are added to the alkali metal silicate in the reactor can be predetermined and is generally based on the volume of the reactor and the difficulties in control of the temperature and agitation. After completion of the addition of the alkali metal silicate solution, the acidulation agent is continually added until the pH of the reaction slurry falls below about 6.0 and preferably to within the range of about 4.6–5.0. The resulting slurry is the precipitated silicon dioxide contained in the reaction medium.

After the pH of below 6.0 is reached, the slurry is then heated for a digestion period to stabilize the surface area at a temperature of 10° to 30° C. above the reaction temperature for about 5 to 15 minutes and the reaction pH again adjusted as necessary. The resulting slurry is then filtered and washed with additional water to remove any reaction by-product such as sodium sulfate which may be contained in the silicon dioxide product. The wet cake moisture of the resulting filter cake is less than about 51% and is a very low structure material.

As pointed out above, also provided by the present invention herein are therapeutic toothpastes or dentifrice compositions containing the instant novel precipitated silicon dioxide abrasives. In addition to the abrasives, the toothpaste compositions also contain certain amounts of a water-soluble fluoride ion source, a binding agent, a humectant system and water. These components are described in more detail as follows.

A. Abrasive

The instant precipitated silicon dioxide abrasive are suitable for incorporation into any type of toothpaste composition and are particularly suitable for use in fluoride-containing therapeutic toothpaste compositions. Therapeutic toothpastes employing such abrasives provide satisfactory tooth cleaning performance and also possess excellent abrasive fluoride compatibility characteristics. The instant toothpaste compositions essentially contain from about 6% to 35%, preferably from about 10% to 20%, by weight of the instant precipitated silicon dioxide abrasives.

B. Fluoride Ion Source

Therapeutic toothpaste compositions will further contain from about 0.01% to 3%, preferably about 0.1% to 1.0%, by weight of a water-soluble, fluorine-containing material which yields fluoride ions in aqueous solutions. Such fluoride ions combine with dental enamel and thereby reduce enamel solubility in acid. Application of fluoride ions to dental enamel serves to protect teeth against decay.

A wide variety of fluoride ion-yielding materials can be employed as sources of soluble fluoride in the instant compositions. Examples of suitable fluoride ion-yielding materials are found in U.S. Pat. No. 3,535,421 and U.S. Pat. No. 3,678,154; the disclosure of both patents being incorporated herein by reference. Preferred fluoride ion sources for use herein include sodium fluoride (NaF), stannous fluoride ($SnF_2$), potassium fluoride (KF), potassium stannous fluoride ($SnF_2$-KF), indium fluoride ($InF_3$), zinc fluoride ($ZnF_2$), ammonium fluoride ($NH_4F$), and stannous chlorofluoride (SnClF). Sodium fluoride and stannous fluoride are particularly preferred as well as mixtures thereof.

C. Binder

A binder is essentially employed to prevent separation of the liquid and solid phases in the toothpaste compositions herein. Such binder materials are well known in the toothpaste art. The most conventionally used binders are the seaweed colloids such as Carrageenan (Irish moss of Viscarin ®) and derivatives of cellulose, such as sodium carboxymethyl cellulose and hydroxyethyl cellulose. Another type of binder which is suitable for use herein are gums such as 1) vegetable gums, e.g., guar gums, and 2) fermentation products, e.g., xanthan gum. The binder component generally comprises from about 0.1% to 5%, preferably 0.2% to 2% by weight of the toothpaste compositions herein. Since the natural and synthetic water dispersions of water binders are subject to microbial or mold attack, the toothpastes herein can optionally contain a relatively small amount of a preservative. Examples of preservatives typically employed are the esters of parahydroxyl benzoates.

D. Humectant

Another essential component of the toothpaste compositions herein is a humectant or humectant system. Suitable humectant materials are also well known in the toothpaste art. The humectant serves to retain moisture and thereby to keep the toothpaste compositions from hardening upon exposure to air. Certain humectants can also impart desirable sweetness or flavor to toothpaste compositions. The humectant generally comprises from about 5% to 55%, preferably from about 20% to 36%, by weight of the toothpaste compositions herein.

Suitable humectants for use in this invention include edible polyhydric alcohols such as glycerine, sorbitol, xylitol and propylene glycol. Sorbitol is frequently employed as a 70% aqueous solution known as Sorbo ®. Mixtures of glycerine and sorbitol are especially preferred as the humectant component of the toothpaste compositions herein.

E. Water

Water is another essential element of the toothpastes of this invention. Water employed in the preparation of commercially suitable toothpastes should be deionized and free of organic impurities. Water comprises from about 15% to 80%, preferably from about 15% to 40%, by weight of the toothpaste compositions herein.

F. Optional Ingredients

In addition to the above described essential components, the toothpastes of this invention can contain a variety of optional conventional toothpaste ingredients. Such optional ingredients include: (1) sudsing agents, (2) pellicle film penetration agents, (3) flavoring and sweetening agents, (4) anticalculus, antiplaque agents, and (5) pigments and coloring agents.

(1) Sudsing Agent

A preferred optional ingredient is a sudsing agent which is present in an amount of about 0.1% to 6% by weight of the total composition. Suitable sudsing agents are those which are reasonably stable and form suds throughout a wide pH range, i.e., nonsoap anionic, non-ionic, cationic, zwitterionic and amphoteric organic synthetic detergents. Sudsing agents of these types are described more fully in U.S. Pat. Nos. 3,959,458 and 3,937,807.

Anionic sudsing agents useful herein include the water-soluble salts of alkyl sulfates having from 8 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be employed.

(2) Phosphate Pellicle Penetration Agent

The toothpaste compositions of the present invention contain, as a highly preferred optional component, from about 5% to 12%, preferably from about 7% to 11%, by weight of a water-soluble phosphate "pellicle penetration agent." Such soluble phosphate salts serve to promote transfer of fluoride ions through the naturally-occurring salivary pellicle film formed on the teeth. Fluoride-containing toothpaste, which utilize the levels of phosphate salts prescribed herein, demonstrate enhanced fluoride pellicle diffusion and dental enamel fluoride uptake in comparison with fluoride toothpastes which contain no such phosphate pellicle penetration agents.

Phosphate salts optionally present in the toothpaste compositions herein are water-soluble. For purposes of this invention, a "water-soluble" phosphate salt is one which is soluble in water to the extent of at least 3.0 g/100 cc $H_2O$ at 20° C.

The phosphates are those phosphorous compounds in the anions of which each atom of phosphorus is surrounded by four oxygen atoms arranged at the corners of a tetrahedron. By sharing oxygen atoms between tetrahedra, chains, rings and branches, polymers of interconnected $PO_4$ tetrahedra can be realized. Simple phosphates are orthophosphates. Polymeric phosphates include the polyphosphates such as the pyrophosphates and tripolyphosphates. Ring phosphates are the metaphosphates.

Examples of suitable water-soluble polyphosphates for use herein include: tetrapotassium pyrophosphate, tetrasodium pyrophosphate, disodium pyrophosphate, sodium tripolyphosphate and potassium tripolyphosphate. Examples of suitable water-soluble metaphosphates include: monopotassium metaphosphate, sodium trimetaphosphates, sodium hexametaphosphate, and sodium heptametaphosphate. Many of these water-soluble polyphosphates and metaphosphates are utilized in the form of hydrated salts.

(3) Flavoring Agents

Flavoring agents can also be added to the instant compositions. Suitable flavoring agents include: oil of wintergreen, oil of peppermint, oil of spearmint, oil of sassafras, and oil of clove. Sweetening agents which can be used include: saccharin, dextrose, levulose, aspartame, D-tryptophan, acetosulpham, dihydrochalcones and sodium cyclamate. Flavoring agents are generally used in toothpastes at levels of from about 0.01% to 2% by weight and sweetening agents at levels of from about 0.05% to about 3% by weight.

(4) Antiplaque/Anitcalculus Agent

Phosphorous-containing anticalculus agents and/or bis-biguanide antiplaque agents can also optionally be added to the toothpastes of this invention. Phosphorus-containing anticalculus agents such as disodium ethane-1-hydroxy-1, 1-diphosphonate and related materials are described more fully in U.S. Pat. No. 3,488,419, incorporated herein by reference. Bis-biguanide antiplaque agents such as chlorhexidine (1,6-bis[$N^5$-p-chlorophenyl-$M^1$-biguanido]hexane), the soluble and insoluble salts thereof and related materials such as 1,2-bis(N[5]-p-trifluoromethylphenyl-N[1]-biguanido) ethane are described more fully in U.S. Pat. Nos. 2,934,002 and 3,937,807.

If present, the optional anticalculus and/or antiplaque agents generally comprise from about 0.01% to 2.5% by weight of the toothpaste compositions herein.

(5) Pigments and Coloring Agents, Misc.

A variety of other optional components well known in the art may be added to the toothpaste compositions herein to improve the usual aesthetics. These include: pigments, dyes, speckles and the like. When present, these optional components generally comprise from about 0.001 to about 2% by weight of the toothpastes herein.

Toothpaste compositions of the present invention are prepared simply by mixing together, in any order and by any conventional means, the essential and optional components herein. Once prepared, the compositions herein provide a pH of from about 4.0 to 8.0, preferably 6.5 to 7.5 when said compositions are slurried with water in a 3:1 weight ratio of water to composition. Fluoride toothpastes providing pH values within the 4.0 to 8.0 range provide especially effective dental enamel antisolubility benefits compared to toothpastes with pH values outside this range. Flavoring of toothpastes within this pH range is also comparatively easy.

COMPOSITION USE

Toothpaste compositions of the present invention are used in conventional manner. The toothpaste compositions or slurries thereof are brushed onto dental surfaces and subsequently rinsed away.

During use of the toothpaste herein in conventional manner, pastes or slurries generally contact dental surfaces for at least about 30 seconds. More preferably, such pastes or slurries contact dental surfaces for at least about 60 seconds.

The following examples are presented to illustrate the present invention, but it is not to be considered as limited thereto. In the following examples, parts are by weight unless otherwise indicated.

EXAMPLES

A fresh water sodium silicate solution having an SiO$_2$/Na$_2$O mole ratio 2.6±0.05 was prepared by the pressure reaction of high purity sand and a 50% by weight NaOH solution. The concentrated sodium silicate solution was diluted with enough fresh water to produce two separate sodium silicate solutions having a concentration of 16.0% and 18.6%, respectively.

A commercially available sulfuric acid of about 93% concentration was diluted with sufficient water to produce a dilute solution of 11.4% by weight of sulfuric acid. Aluminum sulfate solution of 15.4% aluminum sulfate and a specific gravity 1.092 was produced by diluting commercially available concentrated alum with fresh water. An acidulating agent was then prepared by mixing the sulfuric acid solution and alum above such that 100 liters of 11.4% sulfuric acid were mixed with 9 liters of 15.4% aluminum sulfate. This mixed acidification agent was then used for the precipitation of the precipitated silicon dioxides by acidification of the 16.0% and 18.6% sodium silicate solutions.

Using these prepared reactants, eight separate batches of precipitated silicon dioxides, four batches using 16.0% sodium silicate solution, and four batches using 18.6% sodium silicate solution were prepared. The following procedure was used:

For each batch, the fresh water sodium silicate solution consisting of 6.8 liters and 16% and 18.6%, respectively, concentration was added to a 151 liter stainless steel reaction vessel. The reaction medium was then heated to 88° C. Each sodium silicate solution of the respective concentration and the mixed acidification agent were then added simultaneously to the reactor while maintaining the reaction temperature at 88° C. The sodium silicate addition rate was 1308 ml/min and the mixed acidification agent rate was 600 ml/min. The addition of sodium silicate solution was discontinued after 42 minutes but the acidification agent was added until the reaction slurry pH of 6.0 was obtained.

The precipitated silicon dioxide was digested at 100° C. for 10 minutes to stabilize the surface area and the reaction slurry was again adjusted to the final pH 6. The precipitated silicon dioxide was filtered and washed with sufficient water to remove sodium sulfate by-product. The filter cake was reslurried in its own water and adjusted to the desired final pH of about 4.0±1 by adding sulfuric acid. A portion of the filter cake was dried at 105° C. until constant weight to determine the % wet cake moisture.

The filter cake was dried and the dry product milled to the desired degree of fineness and then characterized by the various physical/chemical tests.

The process conditions which were used to prepare the various precipitated silicon dioxide batches are listed in Table I.

TABLE I

| Example Number | Volume Silicate In The Reactor | Acidification Agent Rate, ml/min | % Sodium Silicate Concentration | Final pH |
|---|---|---|---|---|
| 1 | 6.8 liters | 600 | 16.0 | 4.0 |
| 2 | 6.8 liters | 600 | 16.0 | 3.5 |
| 3 | 6.8 liters | 720 | 16.0 | 4.0 |
| 4 | 6.8 liters | 720 | 16.0 | 3.5 |
| 5 | 6.8 liters | 600 | 18.6 | 4.0 |
| 6 | 6.8 liters | 600 | 18.6 | 3.5 |
| 7 | 6.8 liters | 720 | 18.6 | 4.0 |
| 8 | 6.8 liters | 720 | 18.6 | 3.5 |

From the above table it will be noted that the main variations had to do with the acidification agent rate in milliliters per minute, the sodium silicate concentration and the final pH of the mixture. After each of these products were prepared, the resultant dried precipitated silicon dioxides were then characterized and the properties of these silicon dioxides are set forth in the following Table II:

TABLE II

| Example Number | % Wet Cake Moisture | Refractive Index | Oil Absorption cc/100g | Surface Area m$^2$/g | Density, lb/cu.ft. | |
|---|---|---|---|---|---|---|
| | | | | | Pour | Pack |
| 1 | 50.1 | 1.457 | 58 | 285 | 18.9 | 37.8 |
| 2 | 51.2 | 1.457 | 51 | 308 | 18.1 | 34.7 |
| 3 | 50.0 | 1.453 | 50 | 266 | 19.0 | 36.7 |
| 4 | 43.6 | 1.451 | 53 | 275 | 17.6 | 35.2 |
| 5 | 48.4 | 1.460 | 59 | 356 | 16.6 | 34.7 |
| 6 | 50.9 | 1.463 | 57 | 354 | 16.4 | 34.7 |
| 7 | 46.1 | 1.463 | 52 | 374 | 18.1 | 37.2 |
| 8 | 47.4 | 1.463 | 50 | 370 | 18.4 | 37.2 |

The respective precipitated silicon dioxide products were then incorporated into a toothpaste composition for evaluation. The toothpaste formulations were identical except for use of the respective silicon dioxides produced in Examples 1 to 8. Eight formulations were prepared which had the following composition of Table III:

TABLE III

TOOTHPASTE FORMULATION

| Component | Parts By Weight |
|---|---|
| Precipitated Silicon Dioxide Clearing Agent (Examples 1 through 8) | 12.00 |
| Thickener, Precipitated Silica, Zeosyl ® 200 | 10.00 |
| Sorbitol 70% | 52.37 |
| Glycerine 99.5% | 13.60 |
| CMC-7MP | 0.60 |
| Sodium Saccharin | 0.20 |
| Color | 0.60 |
| Sodium Benzoate | 0.08 |
| Flavor | 1.25 |
| Stannous Fluoride | 0.41 |
| SLS/Glycerine (20:80) | 5.89 |
| Carbowax 1500 | 3.00 |
| | 100.00 |

Using this toothpaste formulation, the precipitated silicon dioxide cleaning agents from Examples 1 through 8 were prepared for evaluation for toothpaste characteristics. This toothpaste evaluation data is set forth in the following Table IV:

TABLE IV

TOOTHPASTE EVALUATION DATA

| Toothpaste Containing | Dentifrice RDA* | % Fluoride Compatibility | Toothpaste Clarity** |
|---|---|---|---|
| Silicon Dioxide | | | |
| Example 1 | 350 | 84 | 4 |
| Example 2 | 380 | 85 | 6 |
| Example 3 | 381 | 86 | 4 |
| Example 4 | 325 | 86 | 5 |
| Example 5 | 360 | 83 | 8 |
| Example 6 | 362 | 84 | 9 |
| Example 7 | 364 | 88 | 8 |
| Example 8 | 401 | 87 | 9 |
| Commercial Clear-gel Toothpaste with Xerogel | 300 | 85 | 8 |

*RDA - Radioactive Dentin Abrasion - Grabenstetter et al., Journal of Dental Research 32, 1060 (1958). A calcium pyrophosphate standard was assigned a value of 500.
**Toothpaste Clarity Rating System

| Rating | Description |
|---|---|
| 9-10 | Clear toothpaste, superior to commercial clear-gel toothpaste |
| 8-7 | Clear toothpaste, clarity equal to commercial toothpaste |
| 5-6 | Hazy toothpaste |
| 3-4 | Slightly cloudy toothpaste |
| 1-2 | Cloudy toothpaste |

As can be seen from the data in Table IV, the precipitated silicon dioxides of the present invention, particularly Examples 5 through 8, provide toothpaste clarities in the range of 8 to 9, with RDA values of at least above 350 and fluoride compatibilities of about 85.

The novel precipitated silicon dioxides of the present invention were evaluated in an opaque toothpaste formulation given in Table V.

TABLE V

OPAQUE TOOTHPASTE FORMULATION

| Component | Parts by Weight |
|---|---|
| Precipitated Silicon Dioxide Cleaning Agent (Example 5) | 30.0 |
| Sodium Fluoride (NaF) | 0.22 |
| Glycerine, 99.5% purity | 10.00 |
| Sorbitol Solution, 70% | 20.00 |
| CMC-7MF | 1.00 |
| Monosodium Orthophosphate Monohydrate ($NaH_2PO_4 \cdot H_2O$) | 0.30 |
| Disodium Orthophosphate Dihydrate ($Na_2HPO_4 \cdot 2H_2O$) | 0.30 |
| Sodium Alkyl Sulfate Solution (28.8%) | 2.3 |
| Flavor | 1.0 |
| Sodium Saccharin | 0.20 |
| Titanium Dioxide | 0.50 |
| Deionized Water | Balance |
| TOTAL | 100.00 |

The opaque dentifrice resulted in excellent cleaning properties and 88% fluoride compatibility. The RDA of the dentifrice resulting from the formulation in Table V was 450.

The invention has been described herein with reference to certain preferred embodiments; therefore, as obvious variations will become apparent to those skilled in the art, the invention is not to be considered as limited thereto.

What is claimed is:

1. A synthetic precipitated silicon dioxide that provides a toothpaste clarity of 8 to 9, a radioactive dentin abrasion value of 360 to 401 and a % fluoride compatibility of 83-88 when incorporated into a visually clear toothpaste as an abrasive and cleaning agent, said silicon dioxide being characterized by wet cake moisture of from 46.1 to 50.9, a refractive index ranging from 1.46 to 1.463, an oil absorption ranging from 50 to 59 cc/100 g, a surface area ranging from 354 to 374 $m^2/g$, a pour density ranging from 16.4 to 18.4 lb./cu.ft., and a pack density ranging from 34.7 to 37.2 lb./cu.ft., 2. A synthetic precipitated silicon dioxide according to claim 1 which is characterized by a surface area of about 356 to 374 $m^2/g$.

3. A method for the production of the precipitated silicon dioxide of claim 1 which comprises:
   (a) forming an acidification solution containing a dilute mineral acid in the range of about 10% to 20% by weight, forming an adduct solution containing about 10% to 25% by weight of adduct material, the adduct being selected from the group consisting of a water soluble salt of aluminum, calcium, strontium and barium.
   (b) mixing said mineral acid solution and said adduct solution to form said acidification agent in fresh water;
   (c) forming a fresh water solution of sodium silicate having a concentration of about 18% to 20% by weight;
   (d) charging a portion of the sodium silicate solution to a reactor and bringing to a reaction temperature in the range of about 50° to 90° C., and adding with good agitation the remainder of the sodium silicate solution simultaneously with the acidification agent while maintaining the reaction temperature, the addition rate of the mixed acidification agent being no more than one-half the rate of addition of the sodium silicate portion;
   (e) continuing addition of acidification agent after completion of the addition of the sodium silicate solution to a reaction slurry pH of 6.0;

(f) digesting the resulting precipitated silicon dioxide by heating at 10° to 30° C. above the reaction temperature to stabilize the surface area;
(g) adjusting to the final pH of 6;
(h) filtering the precipitated product and washing with sufficient water to remove by-products;
(i) reslurrying the filter cake in its own water and adjusting to the final pH of 4±1, and drying to constant weight.

4. A method according to claim 3 wherein the adduct material is a dilute solution of aluminum sulfate having a concentration of about 15% to 18% by weight and the sodium silicate solution has a $SiO_2/Na_2O$ mole ratio of about 2.6±0.05.

5. A method according to claim 3 wherein digestion is carried out by heating at a temperature of about 100° C. for about 5 to 15 minutes.

6. A visually clear dentifrice composition containing as an abrasive agent, the precipitated silicon dioxide of claim 1.

7. A dentifrice composition according to claim 6 in the form of a toothpaste.

8. A dentifrice composition according to claim 6 in the form of a visually clear toothpaste wherein the refractive index of the precipitated silicon dioxide substantially matches the refractive index of the liquid phase of the toothpaste to provide a toothpaste of improved transparency.

* * * * *

UNITED STATES PATENT AND TRADEMARK OFFICE
CERTIFICATE OF CORRECTION

PATENT NO. : 4,272,509
DATED : June 9, 1981
INVENTOR(S) : Satish K. Wason

It is certified that error appears in the above—identified patent and that said Letters Patent is hereby corrected as shown below:

Column 6, line 41, "abrasive" should be -- abrasives --.

Column 6, line 59, "enamal" should be -- enamel --.

Column 8, line 17, "toothpaste" should be -- toothpastes --.

Column 8, line 59, "/Anitcalculus" should be -- /Anticalculus --.

Column 11, between lines 10-15, "CMC-7MP" should be -- CMC-7MF --.

Column 11, between lines 40-45, second line of footnotes, "Research 32" should be -- Research 37 --.

Signed and Sealed this

Twenty-second Day of September 1981

[SEAL]

Attest:

GERALD J. MOSSINGHOFF

Attesting Officer

Commissioner of Patents and Trademarks